(12) United States Patent
Hanson et al.

(10) Patent No.: US 10,391,303 B2
(45) Date of Patent: Aug. 27, 2019

(54) TOOLS AND METHODS FOR IMPLANTATION OF IMPLANTABLE MEDICAL LEAD EXTENSIONS OR CATHETERS

(71) Applicant: Medtronic, Inc., Minneapolis, MN (US)

(72) Inventors: Scott M. Hanson, Savage, MN (US); Bruce A. Behymer, Grant, MN (US); Charles T. Bombeck, Lino Lakes, MN (US); Douglas S. Cerny, Minneapolis, MN (US); Darrin E. Dickerson, Blaine, MN (US); Jeffrey R. Dixon, Andover, MN (US); Phillip C. Falkner, Minneapolis, MN (US); Evan M. Gustafson, Golden Valley, MN (US); Raymond F. McMullen, Shorewood, MN (US); Thomas I. Miller, Blaine, MN (US); Joseph P. Ricci, Ham Lake, MN (US); Adam J. Rivard, Blaine, MN (US); Chad C. Whiterabbit, Mahtomedi, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 646 days.

(21) Appl. No.: 14/179,716

(22) Filed: Feb. 13, 2014

(65) Prior Publication Data
US 2014/0276904 A1    Sep. 18, 2014

Related U.S. Application Data

(60) Provisional application No. 61/781,653, filed on Mar. 14, 2013.

(51) Int. Cl.
*A61B 17/00* (2006.01)
*A61N 1/05* (2006.01)
(Continued)

(52) U.S. Cl.
CPC ...... *A61N 1/0551* (2013.01); *A61B 17/00234* (2013.01); *A61B 17/3415* (2013.01); (Continued)

(58) Field of Classification Search
CPC .... A61B 2017/320056; A61B 17/3415; A61B 2017/00477; A61N 1/0551; A61N 1/0504; (Continued)

(56) References Cited

U.S. PATENT DOCUMENTS 5,782,841 A    7/1998   Ritz et al.
6,605,094 B1   8/2003   Mann et al.
(Continued)

*Primary Examiner* — Katrina M Stransky
*Assistant Examiner* — Lindsey Bachman
(74) *Attorney, Agent, or Firm* — Withers & Keys, LLC

(57) ABSTRACT

Tips for use on a tunneling tool provide the ability to pull an implantable medical lead extension or catheter body through a subcutaneous tunnel. The tips may include a pin with a barb, where the barb is inserted within a compliant portion of a connector body of the lead extension or a catheter body to create an interference fit that allows the connector body or catheter body to be pulled through the tunnel. The tips may include a carrier that has a cavity for the connector body, where the tunneling is performed with the carrier present on the tunneling tool. A body is positioned within the cavity of the carrier to prevent tissue from snagging on and collecting within the carrier. The body may include a tip portion that performs the tunneling function. The carrier may also provide tunneling and/or may be attached to the tunneling tool during tunneling.

11 Claims, 21 Drawing Sheets

(51) Int. Cl.
*A61B 17/34* (2006.01)
*A61M 25/01* (2006.01)
*A61M 25/06* (2006.01)
*A61B 17/32* (2006.01)
*A61M 25/00* (2006.01)

(52) U.S. Cl.
CPC .... *A61M 25/0194* (2013.01); *A61M 25/0662* (2013.01); *A61B 2017/0046* (2013.01); *A61B 2017/320056* (2013.01); *A61M 25/0068* (2013.01); *A61M 25/0069* (2013.01)

(58) Field of Classification Search
CPC ..... A61N 1/0558; A61M 39/10; A61M 39/12; A61M 25/0068; A61M 25/0069; A61M 25/0102; A61M 25/0114; A61M 25/0194; A61M 39/14; A61M 2039/1044; A61M 2039/1077
USPC .......................................... 606/129; 604/533
See application file for complete search history.

(56) References Cited

U.S. PATENT DOCUMENTS

| | | | |
|---|---|---|---|
| 7,537,245 B2* | 5/2009 | Cross, Jr. | A61M 39/1011 |
| | | | 285/114 |
| 8,355,787 B2 | 1/2013 | Barker et al. | |
| 2007/0078396 A1* | 4/2007 | Feeley | A61B 17/3415 |
| | | | 604/164.01 |
| 2007/0173879 A1* | 7/2007 | Pandey | A61B 17/06109 |
| | | | 606/190 |
| 2008/0097409 A1* | 4/2008 | Stephens | A61B 17/3415 |
| | | | 604/533 |
| 2009/0030426 A1 | 1/2009 | Zinn et al. | |
| 2012/0016377 A1 | 1/2012 | Geroy | |
| 2012/0059321 A1 | 3/2012 | Hammond et al. | |
| 2012/0083794 A1 | 4/2012 | Martin et al. | |
| 2012/0191106 A1 | 7/2012 | Ko et al. | |
| 2012/0284991 A1* | 11/2012 | Kusz | A61M 39/10 |
| | | | 29/428 |

* cited by examiner

TOOLS AND METHODS FOR IMPLANTATION OF IMPLANTABLE MEDICAL LEAD EXTENSIONS OR CATHETERS

TECHNICAL FIELD

Embodiments relate to the implantation of implantable lead extensions or catheters. More particularly, embodiments relate to kits and related methods used when implanting an implantable lead extension.

BACKGROUND

When a patient is a candidate for an implantable therapy, an implantable lead or catheter may be implanted and a lead extension or a catheter extension may also be necessary depending upon the location of the therapy site. For example, with stimulation therapy such as sacral nerve stimulation therapy, spinal cord stimulation therapy and the like that may be used to treat conditions such as incontinence or chronic pain, it is often desirable to conduct a trial period of stimulation. This trial period allows an external stimulator to be used so that the patient is not required to undergo a full stimulation device implantation procedure but calls for a lead extension to extend between the lead and the external stimulator. If the trial is successful, then an implantable stimulator is fully implanted into the patient.

When implanting the trial system, an implantable medical lead is implanted with a distal end being routed to the stimulation site. The proximal end of the lead is routed to a pocket away from the entry site. An implantable lead extension is typically then routed subcutaneously from the location of the proximal end of the implanted medical lead to an exit site nearby the location where the external stimulator will be mounted to the patient. An external lead extension is then used to interconnect the exposed proximal end of the implantable lead extension to the external stimulator. Alternatively, the implantable lead extension may be provided with enough length to reach the external stimulator and is further provided with a connector for direct connection to the external stimulator.

During the implantation of the lead extension or a catheter extension, the lead extension or catheter extension is pulled through a subcutaneous tunnel. One manner of doing this is to utilize a carrier on the end of the tunneling tool, where a connector body of the lead extension is placed within a cavity of the carrier. However, this requires the carrier to be removed from the tunneling tool during the tunnel creation to avoid the cavity of the carrier snagging on and collecting tissue and then attached prior to pulling the lead extension through the tunnel. This adds unwanted steps to the surgical procedure. Another approach is to place a cover around the carrier while the carrier is on the tunneling tool, but in some cases the approach creates a larger diameter around the carrier during tunneling which may make the tunneling process more difficult.

Rather than a carrier, a pin located on the tunneling tool may be inserted into a lead bore of the connector but this requires a set screw or other fastener to be manually tightened onto the pin in order to create an engagement of the pin to the connector which further complicates the implantation procedure. Furthermore, the pin does not provide adequate coupling in order to successfully pull a catheter extension through a subcutaneous tunnel.

SUMMARY

Embodiments address issues such as these and others by providing tools and methods that allow for the connector and associated lead extension or for the catheter extension to be pulled through the subcutaneous tunnel while alleviating issues associated with using a pin or carrier. With respect to a pin, features such as a barb are present at the pin to create an interference fit with a compliant portion of the connector body or catheter extension body so that the pin does not require any further manipulation to engage the connector body during the pull-through procedure. With respect to a carrier, embodiments provide a body that is positioned within the cavity to prevent tissue from snagging or being collected during tunneling, where the body is then easily removed from the cavity. Furthermore, the body may provide a tip portion that performs the tunneling action.

Embodiments provide a tool for pulling an implantable medical lead extension through a subcutaneous tunnel. The tool includes a handle and a shaft having a first end and a second end with the first end being coupled to the handle. The tool further includes a pull-through tip coupled to the second end of the shaft, the tip comprising a pin having an end that is sized to be inserted into a bore of a connector body located on a distal end of the implantable lead extension. The tip further includes a barb positioned on the pin and spaced axially from the end of the pin, the barb being sized to create an interference fit within a compliant distal portion of the connector body.

Embodiments provide an assembly that includes an implantable medical lead extension having a connector body located on a distal end, the connector body defining a bore and a compliant distal portion. The assembly further includes a pull-through tip comprising a pin having an end that is present within the bore of the connector body, the tip further comprises a barb positioned on the pin and spaced axially from the end of the pin. The barb has an interference fit within the compliant distal portion of the connector body.

Embodiments provide a method of implanting an implantable medical lead extension. The method involves providing a tool that has a shaft that is located within a subcutaneous tunnel between a first incision and a second incision in a patient with a handle on one end of the shaft that is present externally of the subcutaneous tunnel in proximity to the first incision. A pull-through tip is on the other end of the shaft and is present externally of the subcutaneous tunnel in proximity to the second incision, wherein the tip comprises a pin having an end and a barb positioned on the pin and spaced axially from the end of the pin. The method further involves inserting the pin into a bore of a connector body located on a distal end of the implantable lead extension while inserting the barb within a compliant distal portion of the connector body to create an interference fit of the barb to the compliant distal portion. The method also involves pulling the tool including the tip through the subcutaneous tunnel and out of the first incision to thereby pull the connector body and the implantable lead extension through the subcutaneous tunnel. Additionally, the method involves, after pulling the tool out of the first incision, removing the pin from the bore of the connector body while removing the barb from within the compliant distal portion.

Embodiments provide a tool for pulling an implantable medical lead extension through a subcutaneous tunnel. The tool includes a handle and a shaft having a first end and a second end, the first end being coupled to the handle. The tool further includes a pull-through tip coupled to the second end of the shaft, the tip comprising a carrier body that forms a partial cylindrical wall with a cavity being defined by the partial cylindrical wall. The tool also includes a body that is removably positioned within the cavity that creates an interference fit against an inner surface of the partial cylindrical wall.

Embodiments provide a method of implanting an implantable medical lead extension that involves providing a tool that has a shaft that is located within a subcutaneous tunnel between a first incision and a second incision in a patient with a handle on one end of the shaft that is present externally of the subcutaneous tunnel in proximity to the first incision. A pull-through tip is on the other end of the shaft and is present externally of the subcutaneous tunnel in proximity to the second incision. The tip comprises a carrier body that forms a partial cylindrical wall with a cavity being defined by the partial cylindrical wall and wherein a body is positioned within the cavity and creates an interference fit against an inner surface of the partial cylindrical wall. The method further involves removing the body from the cavity and inserting the connector body located on a distal end of the implantable lead extension into the cavity. Additionally, the method involves pulling the tool including the tip through the subcutaneous tunnel and out of the first incision to thereby pull the connector body in the cavity and the implantable lead extension connected to the connector body through the subcutaneous tunnel. The method also involves, after pulling the tool out of the first incision, removing the connector body from the cavity.

Embodiments provide a tool for pulling an implantable medical lead extension through a subcutaneous tunnel. The tool includes a handle and a shaft having a first end and a second end, the first end being coupled to the handle. The tool further includes a tip coupled to the second end of the shaft, the tip comprising a carrier body that forms a partial cylindrical wall with a cavity being defined by the partial cylindrical wall, the carrier body defining a longitudinal slot and a lateral groove about the circumference of the carrier. The tool also includes a conical tunneling cover with a large diameter end seated in the groove so as to be able to swivel between an open position that exposes the longitudinal slot and a closed position that covers the longitudinal slot.

Embodiments provide a tool for pulling an implantable medical lead extension through a subcutaneous tunnel. The tool includes a handle and a shaft having a first end and a second end, the first end being coupled to the handle. The tool further includes a tip coupled to the second end of the shaft, the tip comprising a conical portion having a longitudinal slot extending through an area of maximum diameter of the conical portion, the slot being sized to receive a distal connector of the lead extension.

Embodiments provide a tool for pulling an implantable medical lead extension through a subcutaneous tunnel. The tool includes a handle and a shaft having a first end and a second end, the first end being coupled to the handle. The tool further includes a tip coupled to the second end of the shaft, the tip comprising a carrier body that includes a first end defining a receptacle that receives a first end of a connector of the lead extension, a second end defining a receptacle that receives a second end of the connector, and a strip interconnecting the first end and the second end.

Embodiments provide a tool for pulling an implantable medical lead extension through a subcutaneous tunnel. The tool includes a handle and a shaft having a first end and a second end, the first end being coupled to the handle. The tool further includes a tunneling tip coupled to the second end of the shaft and a carrier that is removably attached to the shaft while being tethered to the shaft.

Embodiments provide a tool for pulling an implantable medical lead extension through a subcutaneous tunnel. The tool includes a handle and a shaft having a first end and a second end, the first end being coupled to the handle. The tool further includes a tunneling tip coupled to the second end of the shaft and a carrier that is removably attached to the shaft while being pivotably coupled to the shaft.

Embodiments provide a tool for pulling an implantable medical catheter extension through a subcutaneous tunnel. The tool includes a handle and a shaft having a first end and a second end, the first end being coupled to the handle. The tool further includes a tip coupled to the second end of the shaft, the tip comprising a pin having an end that is sized to be inserted into a bore of a catheter extension body, the tip further comprising a barb positioned on the pin and spaced axially from the end of the pin, the barb being sized to create an interference fit within a compliant portion of the catheter extension body.

DETAILED DESCRIPTION

Embodiments provide tips for tunneling tools to aid in the implantation of implantable medical lead extensions. A tip that includes a pin and a barb allows the connector body to be engaged for the pull-through procedure by inserting the pin and barb into the connector body. A tip that includes a carrier with a cavity has a body positioned within the cavity during tunneling which is easily removed after tunneling to allow the connector body to then be installed into the cavity for the pull-through procedure.

Figure 1:
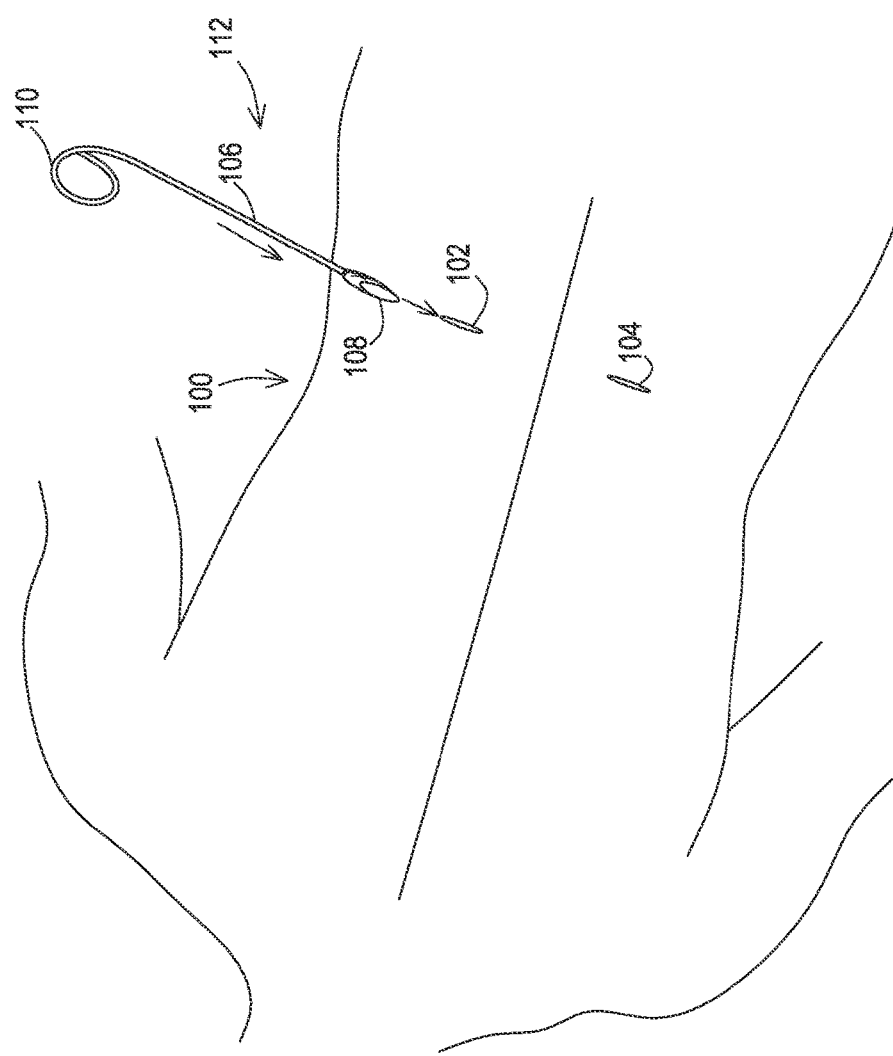
FIG. 1 shows an exemplary first stage of an implantation procedure where a tunnel is being created using a tunneling tip mounted to a tunneling rod tool.

FIG. 1 shows a first stage of an implantation procedure within a typical operating environment for the various embodiments. Here, there are two surgical incisions 102, 104 made in the patient 100. Incision 102 is in proximity to the proximal end of the implantable lead, which may have already been routed within the patient 100 to the internal stimulation site. Incision 104 is in proximity to the intended mounting location of the external stimulator. Incision 104 is used as the externalizing exit site of a lead extension. The lead extension is externalized to connect to the external stimulator. Tunneling away from incision 102 reduces the chance of infection at the incision 102 during the trialing period.

A tunneling tool tip 108 is installed onto an end of a tunneling tool shaft 106 that is coupled to a handle 110 of a tunneling tool 112 being manipulated by the surgeon. The handle and the shaft may be of a unitary construction as shown. The tunneling tool tip 108 may attach to the end of the tunneling tool shaft 106 in various ways, such as by having an end that is threaded onto matching threads present on an end of the tunneling tip 108. The tunneling tool tip 108 may be of various forms such as a removable trocar tip. As an alternative, the tunneling tool tip may be a carrier for receiving the connector body of the lead extension where the carrier has a cavity that includes a body temporarily filling the cavity during tunneling. This body may provide the tunneling tip that creates the tunnel in the tissue. Examples of such a tunneling tip 108 are discussed in more detail below with reference to FIGS. 7-12.

As shown in FIG. 1, the tunneling tip 108 is then inserted through the incision 102 and is forced subcutaneously by the tunneling rod 106 and by skillful manipulation from the surgeon until exiting through the incision 104. This effectively creates a tunnel through fatty tissue between the incision 102 and the incision 104.

Figure 2:
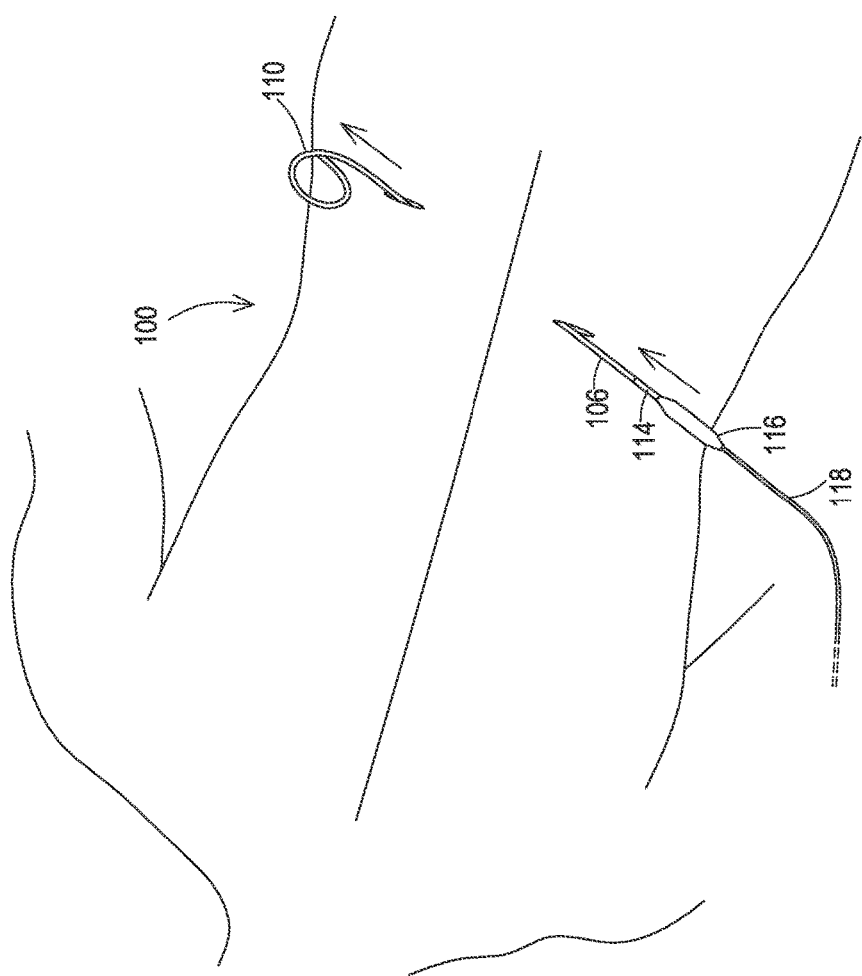
FIG. 2 shows an exemplary second stage of the implantation procedure where an implantable lead extension is pulled through the tunnel using a pull-through tip that is mounted to the tunneling rod.

As shown in FIG. 2, in some embodiments the tunneling tool tip 108 is removed while a separate pull-through tip 114 is installed on the end of the tunneling tool shaft 106. The pull-through tip 114 may be of various forms such as a pin that is inserted into the lead bore of the connector body 116 of the lead extension 118. Alternatively, the connector body 116 may provide a bore that is dedicated to the tunneling procedure such that the pull-through tip 114 in the form of a pin is inserted into the dedicated bore. Examples of the pin are discussed below in more detail with reference to FIGS. 4-6.

At this stage of the implantation procedure shown in FIG. 2, the surgeon pulls the tunneling tool 112 via the handle 110 back through the tunnel between the incisions 102 and 104. Because the connector body 116 is coupled to the tip 114 of the tool 112, the connector body 116 and the lead extension 118 are also pulled through the incision 104 and the tunnel. Once the connector body 116 and lead extension 118 have exited the incision 102, the connector body 116 is then freed from the tip 114.

Figure 3:
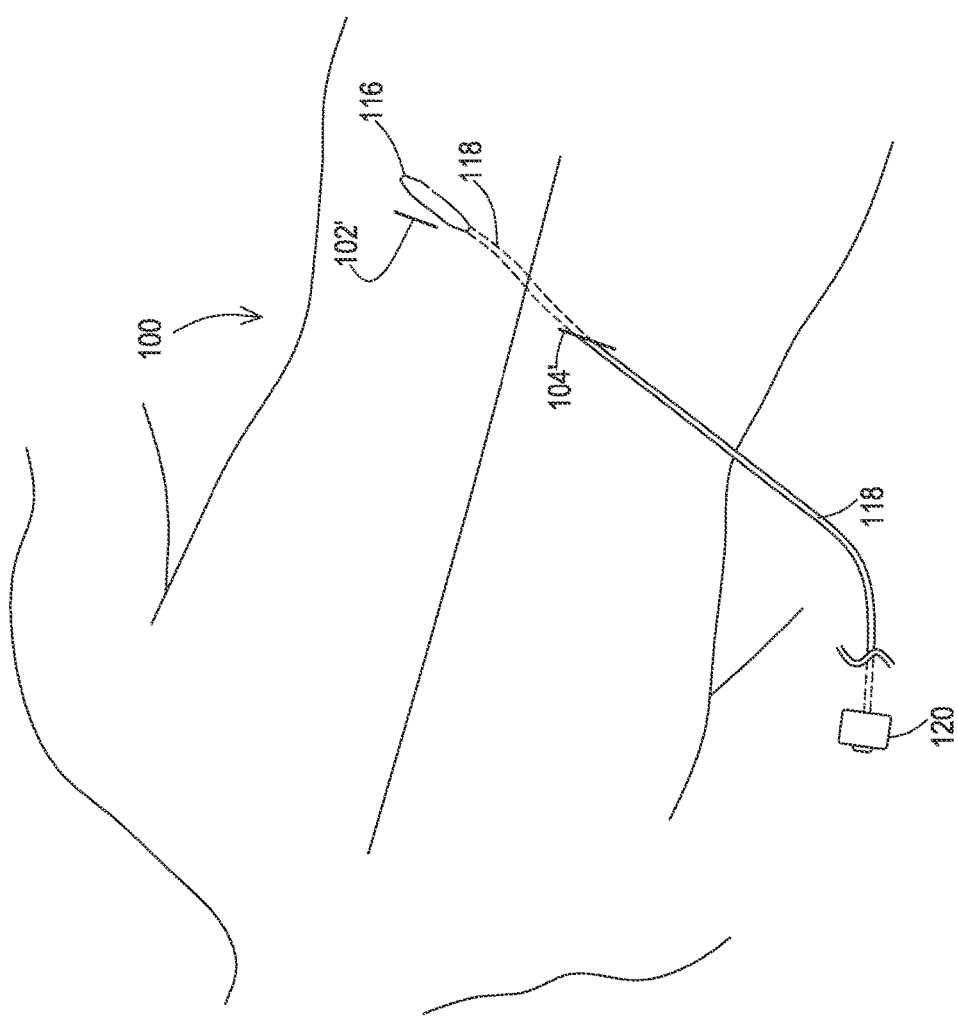
FIG. 3 shows an exemplary third state of the implantation procedure where the implantable lead extension is ready for connection to an external stimulator.

A subsequent stage of the implantation procedure is shown in FIG. 3. Here, the incisions 102', 104' are closed with the implantable lead extension 118 exiting the closed incision 104'. The connector body 116 has been connected to the proximal end of the implanted lead (not shown) and is stored subcutaneously beneath the closed incision 102'. A proximal connector 120 of the implantable lead extension is available for connection to an external extension in some embodiments or directly to an external stimulator 120 in other embodiments.

Figure 4:
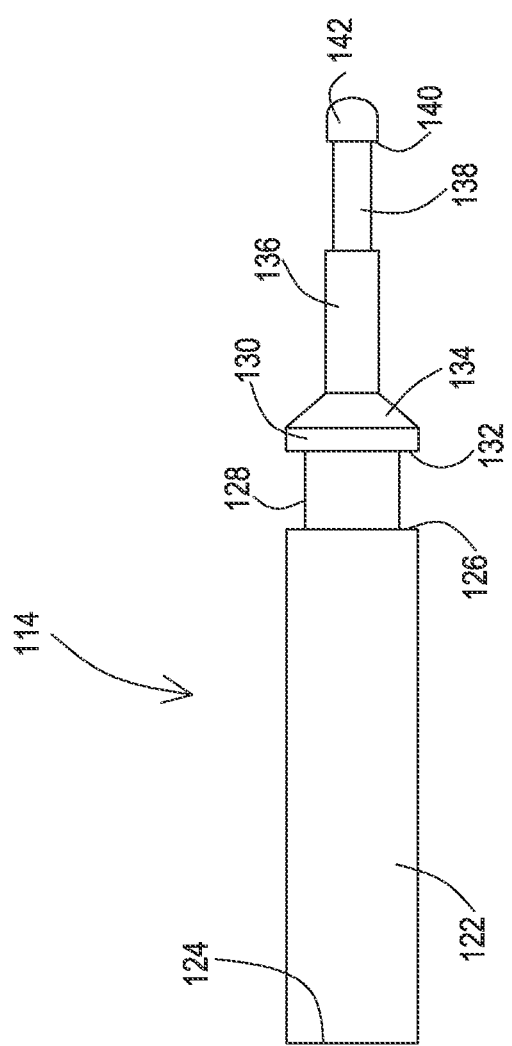
FIG. 4 shows an exemplary first example of a tip for a tunneling rod tool that includes a pin with a barb to create an interference fit with the connector body.
Figure 6:
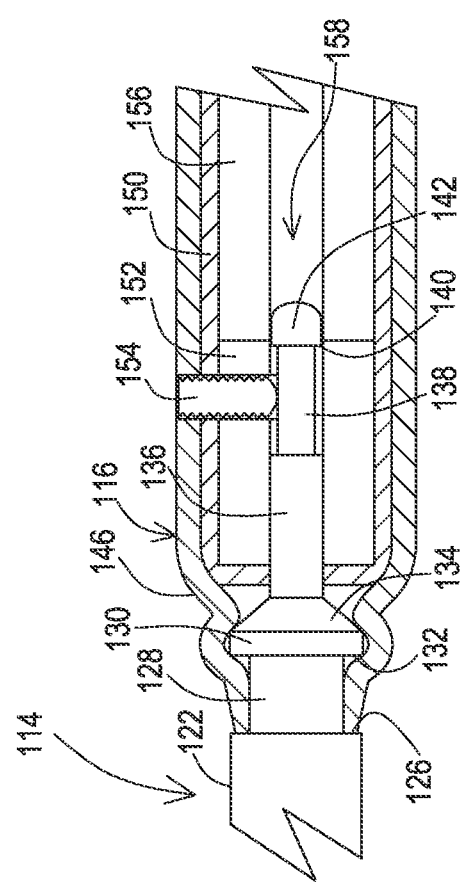
FIG. 6 shows an exemplary cross-sectional view of a connector body with the tip including the pin and barb inserted into the connector body.

FIG. 4 shows an example of a tunneling tool tip that is a pin 114 such as the pin 114 discussed above in relation to FIG. 2. The pin 114 is attached to the shaft 106 on one end 124 such as by a threaded engagement and engages the connector body 116 on the opposite end. FIG. 6 shows the pin 114 of FIG. 4 once inserted into the connector body 116, which is shown in cross-section.

This pin 114 has a barb 130 that is present between the two ends. The barb 130 of this example has a tapered side 134 and a blunt side 132 forming a shoulder. This configuration of the barb 130 allows the barb to more easily enter into an opening in the compliant region 146 of the connector 116 by having the tapered side 134 allows the compliant region 146 to gradually slide onto and over the barb 130. This compliant region 146 may be constructed of a compliant material such as liquid silicone rubber which may serve as an overmold to the underlying structures of the connector body 116 such as a connector carrier 150 and bore components 156 such as seals and electrical connectors. Once within the compliant region 146, the blunt side 132 of the barb 130 creates a snug interference fit that allows the pin 114 to be pulled through the subcutaneous tunnel while maintaining the coupling to the connector body 116. This coupling results in the connector body 116 and lead extension 118 also being pulled through the tunnel without requiring any further efforts by the surgeon to secure the pin 114 to the connector body 116. This saves the surgeon from spending time and effort to tighten a set screw or other manual fixation mechanism.

Figure 5:
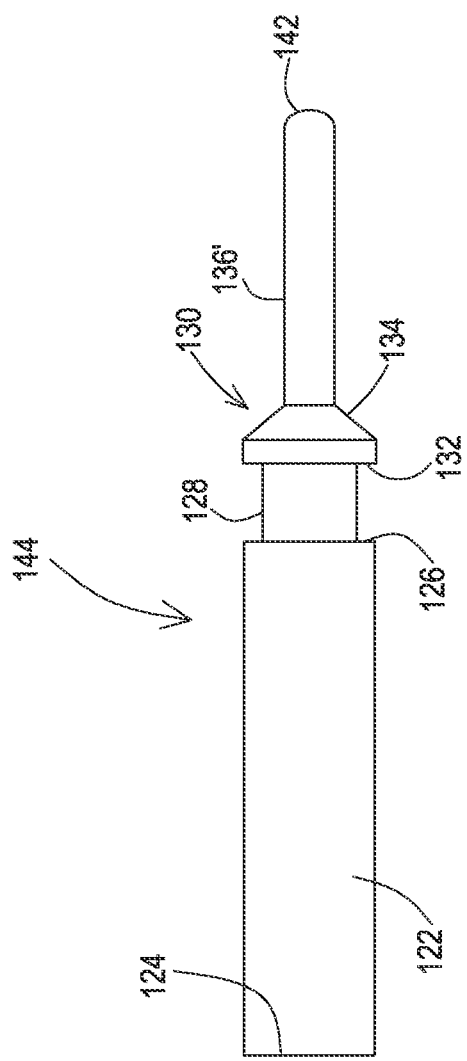
FIG. 5 shows an exemplary second example of a tip for a tunneling rod tool that includes a pin with a barb to create an interference fit with the connector body.

The embodiment of a pin 144 as shown in FIG. 5 also has the barb 130 with the tapered side 134 and the blunt side 132 forming a shoulder. Thus, the barb 130 of the pin 144 enters the opening of the compliant region 146 and then creates a snug interference fit with the compliant region 146 in the same manner as the embodiment shown in FIG. 4.

The pin embodiments of FIGS. 4 and 5 also have a first section 136, 136' with a first diameter on the tapered side of the barb 130 and have an end 142 with the same diameter as the first section 136, 136'. However, the pin 114 has a second section 138 between the first section 136 and the end 142 which has a second diameter that is less than the first diameter, which results in a shoulder 140. This section 138 provides an area where a set screw 154 of a set screw block 152 may be tightened against while a shoulder 140 is engages the set screw 154 if the pin 114 is being pulled outward from the connector body 116 to prevent the escape of the pin 114. Thus, this section 138 may be included to provide surgeons with the option of creating an even more secure engagement of the pin 114 to the connector body 116 if they choose not to rely solely on the engagement by the barb 130. While the pin 144 of FIG. 5 does not include the reduced diameter section 138, a surgeon may also opt to tighten a set screw against the section 136' if so desired to provide additional security of the engagement.

The first section 136, 136' and the end 142 enters a lead bore 158 within the connector body 116 and resides there during the pull-through stage of implantation. Thus, the pin 114, 144 is stabilized to prevent to lateral movements that might tend to dislodge the barb 130. Rather than the lead bore 158, the connector body 116 may provide a separate bore dedicated to the tunneling procedure and the pin 114, 144 may instead be inserted in to the dedicated bore where a compliant portion of the dedicated bore engages the barb 130 to thereby apply the pulling force to the connector body.

The pin 114, 144 also includes a third section 122 having a third diameter and a fourth section 128 having a fourth diameter that is smaller than the third diameter. This allows the opening of the compliant region 146 to close upon the fourth section while abutting the blunt end 126 of the third section 122. In this manner, the shoulder created by the blunt end 126 serves as a stop during insertion of the pin 114, 144 into the connector body 116 and provides confirmation that the pin 114, 144 has been inserted the proper distance. In this particular embodiment, the third diameter of the third section 122 is approximately equal to the diameter of the barb 130, while the fourth diameter of the fourth section 128 is larger than the first diameter of the first section 136, 136', although these diameters may vary for various embodiments.

In these examples, the pin 114, 144 may be made of various biocompatible materials such as metals or rigid plastics. Examples of such materials include Stainless Steel, Polyether ether ketone (PEEK), and Titanium.

Once the pull-through stage of the implantation is complete, the pin 114, 144 is then removed by simply pulling with an amount of force that is capable of overcoming the interference fit cause by the blunt side 132 against the compliant region 146. This amount of force is greater than the amount of drag created on the connector body 116 by the tissue surrounding the tunnel but is still small enough to be easily achieved manually by a surgeon. If a set screw 154 was tightened against the pin 114, 144, then the set screw 154 is released prior to pulling the pin 114, 144 free from the connector body 116.

Figure 7:
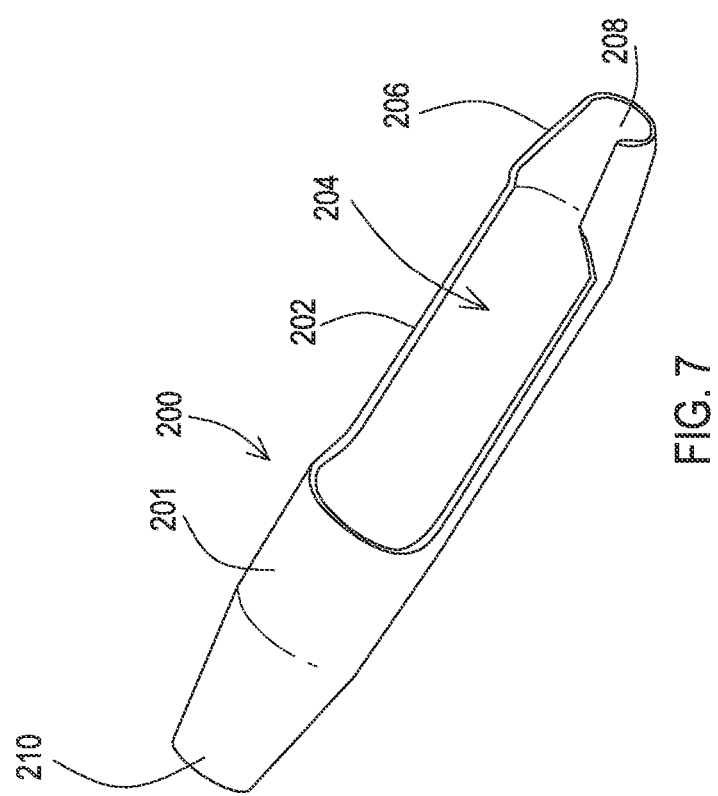
FIG. 7 shows an exemplary tip for a tunneling rod tool that is a carrier that includes a cavity for the connector body.

FIG. 7 shows an alternative tip for the tunneling tool 112. This tip is in the form of a carrier 200 which as an end 210 that attaches to the end of the shaft 106 of the tool 112 such as by a threaded engagement. The carrier 200 includes a portion 201 that forms a hollow, tapered cylinder. Another portion 204 is formed by walls that form only a partial cylinder which exposes a cavity 204 within the carrier. The cavity 204 is shaped and sized roughly the same as the outer dimensions of the connector body 116. A section 206 also forms a hollow, tapered partial cylinder and defines a passageway 208 that accommodates the lead extension 118 extending away from the connector body 116 once the connector body 116 is positioned within the cavity 204.

Prior to positioning the connector body 116 within the cavity, the carrier 200 may be installed on the end of the shaft 106 of the tool 112 during the tunneling stage of the implantation procedure. This eliminates the surgeon from having to attach the carrier 200 to the shaft 106 after tunneling, but the cavity 204 must be isolated from the tissue during the tunneling. Also, there must be a structure for creating the tunnel ahead of the carrier 200.

Figure 8:
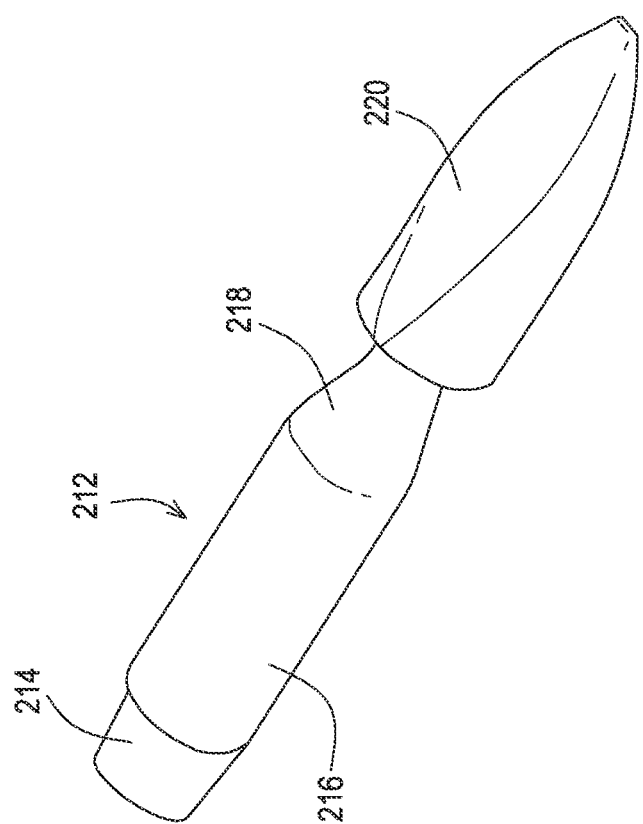
FIG. 8 shows an exemplary first view of a first example of a body to be positioned within the cavity of the carrier during tunneling.
Figure 9:
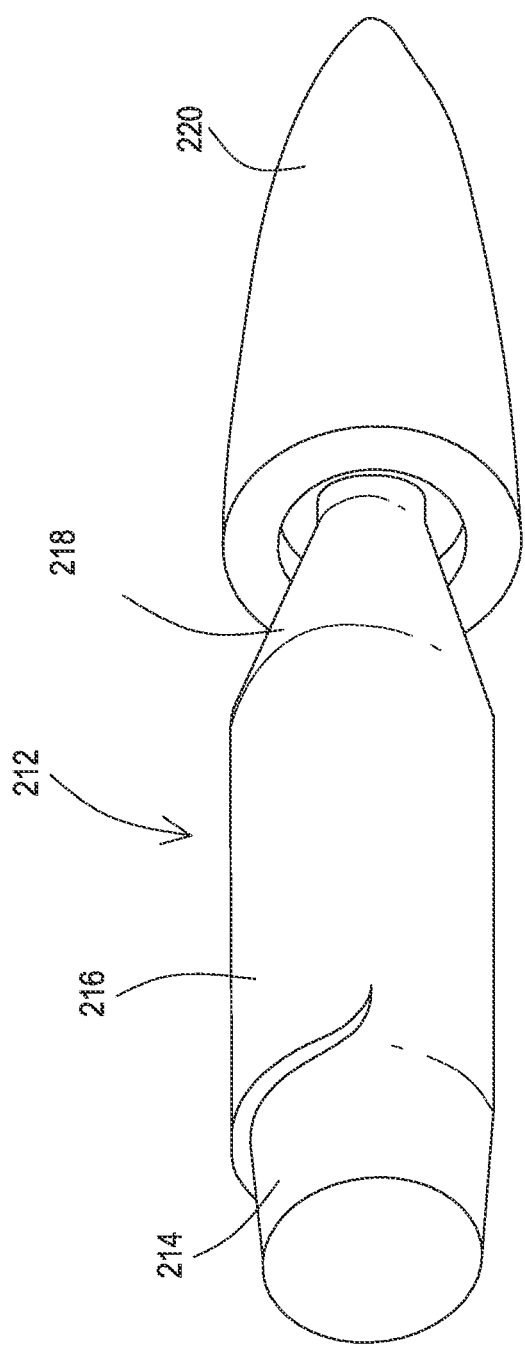
FIG. 9 shows an exemplary second view of the body of FIG. 8.

FIGS. 8 and 9 show a body 212 that fulfills those needs. The body 212 includes a portion 214, a portion 216, and a portion 218 that are a close match in size and shape to the connector body 116. Thus, these portions 212, 214, and 216 of the body 212 achieve an interference fit within the cavity 204.

In this embodiment, the body 212 also includes a tip portion 220 that provides a tunneling function. Thus, during tunneling with the tool 112, the carrier 200 is present with the body 212 residing in the cavity 204 to prevent tissue from snagging on and collecting within the cavity 204 while the tip portion 220 tunnels through the tissue to create the tunnel that the carrier 200 is passing through.

Figure 10:
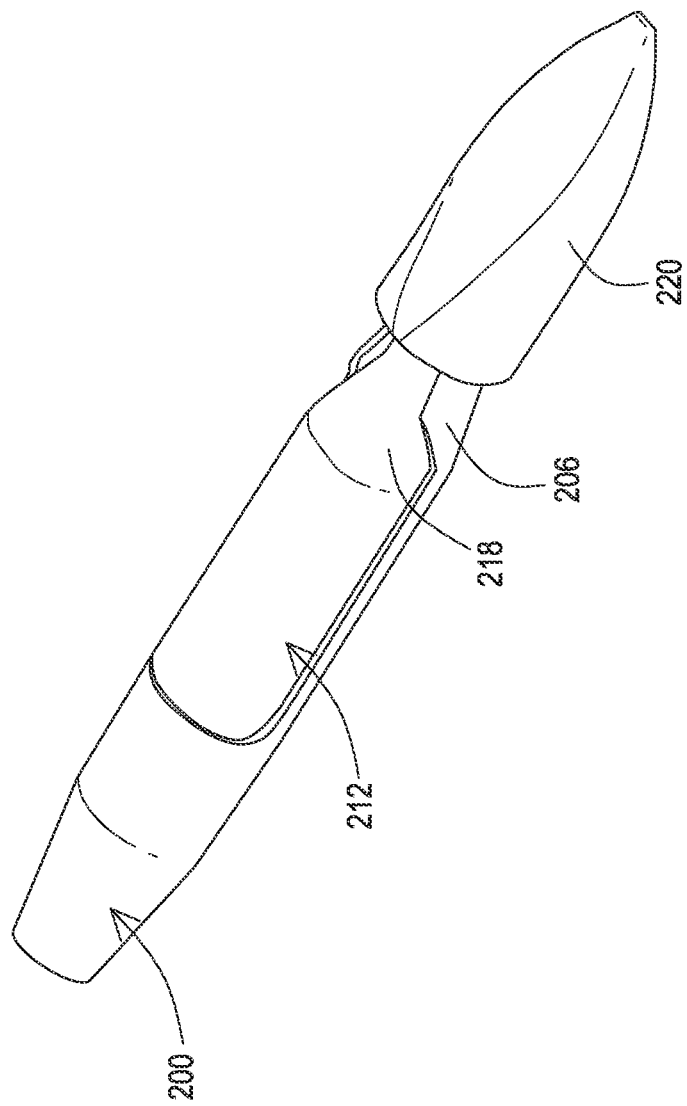
FIG. 10 shows the body of FIG. 8 positioned within the cavity of the carrier.

FIG. 10 shows the carrier 200 with the body 212 present within the cavity 204 and with the tip portion 220 present ahead of the carrier 200. As can be seen, both the portion 206 and the portion 206 of the carrier 200 aid in retaining the body 212 within the cavity 204 via the interference fit. This fit allows the surgeon to then press laterally on the tip portion 220 to remove the body 212 from the cavity 204 once tunneling is complete.

Figure 11:
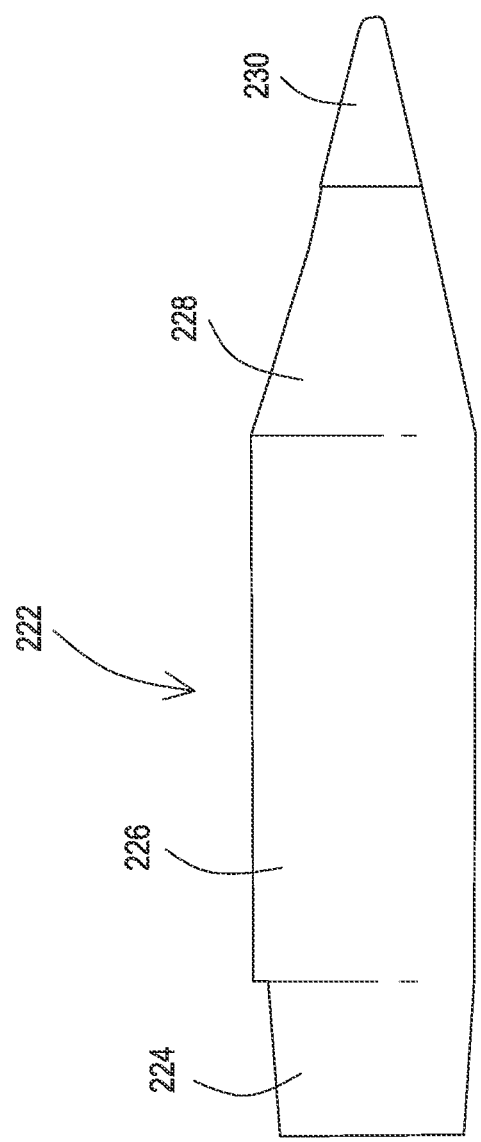
FIG. 11 shows an exemplary second example of a body to be positioned within the cavity of the carrier during tunneling.

FIG. 11 shows another example of a body 222 that addresses the issues presented by the carrier 200 during tunneling. The body 222 includes a portion 224, a portion 226, and a portion 228 that are a close match in size and shape to the connector body 116. Thus, these portions 222, 224, and 226 of the body 222 also achieve an interference fit within the cavity 204.

In this embodiment, the body 222 also includes a tip portion 230 that provides a tunneling function. Thus, during tunneling with the tool 112, the carrier 200 is present with the body 222 residing in the cavity 204 to prevent tissue from snagging on and collecting within the cavity 204 while the tip portion 230 tunnels through the tissue to create the tunnel that the carrier 200 is passing through.

Figure 12:
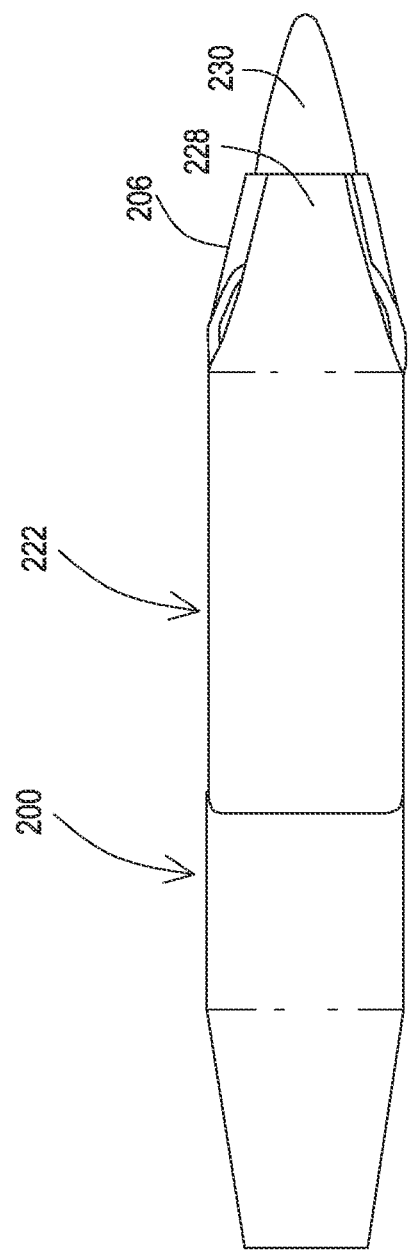
FIG. 12 shows the body of FIG. 11 positioned within the cavity of the carrier.

FIG. 12 shows the carrier 200 with the body 222 present within the cavity 204 and with the tip portion 230 present ahead of the carrier 200. As can be seen, both the portion 206 and the portion 206 of the carrier 200 aid in retaining the body 222 within the cavity 204 via the interference fit. This fit allows the surgeon to then press laterally on the tip portion 230 to remove the body 222 from the cavity 204 once tunneling is complete. Because the tip portion 230 is smaller in diameter at its broadest point than the carrier 200, this embodiment relies on the tapered portion 206 of the carrier 200 to also push away tissue that the tip portion 230 is penetrating during the tunneling.

Accordingly, the combination of the carrier 200 and body 212 or carrier 200 and body 222 may serve as the tip 108 as shown in FIG. 1. Thereafter, the body 212 or 222 is removed. Furthermore, the carrier 200 may serve as a tip that engages the connector body 116 for pulling the connector body into the incision 104 and through the tunnel as shown in FIG. 2.

In these examples, the carrier 200 may be made of various biocompatible materials such as metals or rigid plastics. Examples of such materials include Stainless Steel, Delrin®, PEEK, Titanium. Similarly, the body 212, 222 may also be made of various biocompatible materials such as metals or rigid plastics. Examples of such materials also include Stainless Steel, Delrin®, PEEK, Titanium.

Figure 13:
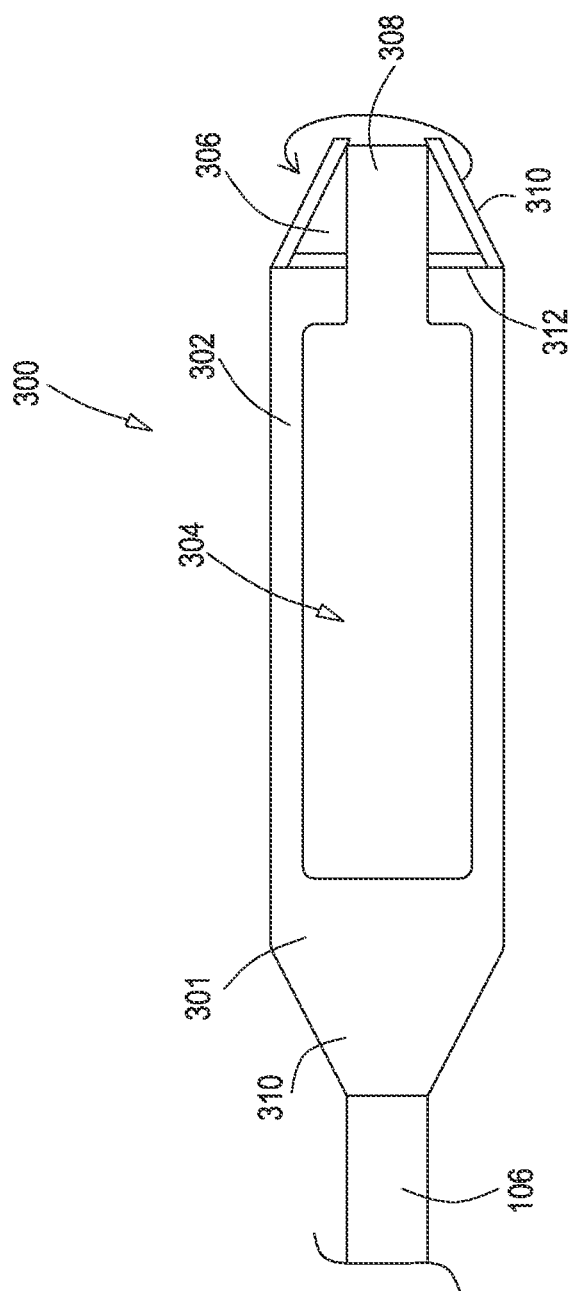
FIG. 13 shows an example of a carrier having a swivel tip in an open position to allow an extension to be inserted.
Figure 14:
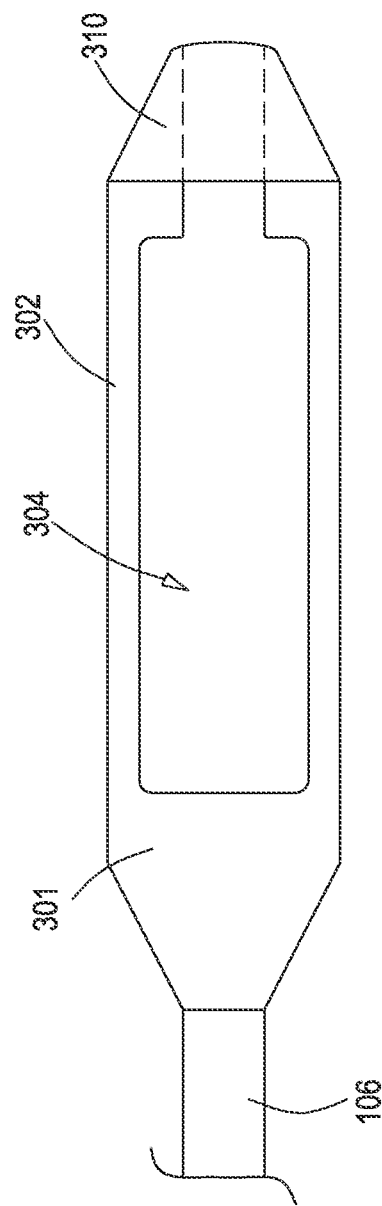
FIG. 14 shows the example of FIG. 13 with the swivel tip in a closed position to provide a tunneling function.

FIG. 13 shows an example of a tip in the form of a carrier 300 that is attached to the shaft 106. The carrier 300 includes a body 302 defining a cavity 304 with a portion 301 on one end and a portion 306 on the opposite end for holding the connector within the cavity 304. The portion 306 includes a longitudinal slot 308 for allowing the elongated portion of the extension lead to pass through. A conical cover 310 is positioned about the portion 306 where an end of the conical cover 310 is seated within a lateral groove 312 about the circumference of portion 306. This allows the cover 310 to swivel from an open position to expose the slot 308 as in FIG. 13 to a closed position to cover the slot 308 as in FIG. 14.

Closing the cover 310 over the slot 308 allows the cover 310 to provide a tunneling function such that the carrier 300 remains installed during tunneling. Once tunneled, the cover 310 may then be swiveled to the open position to expose the slot 308 and to allow the connector of the lead extension to be loaded into the cavity 304 with the elongated portion passing through the slot 308 in preparation for the pull-through procedure.

Figure 15:
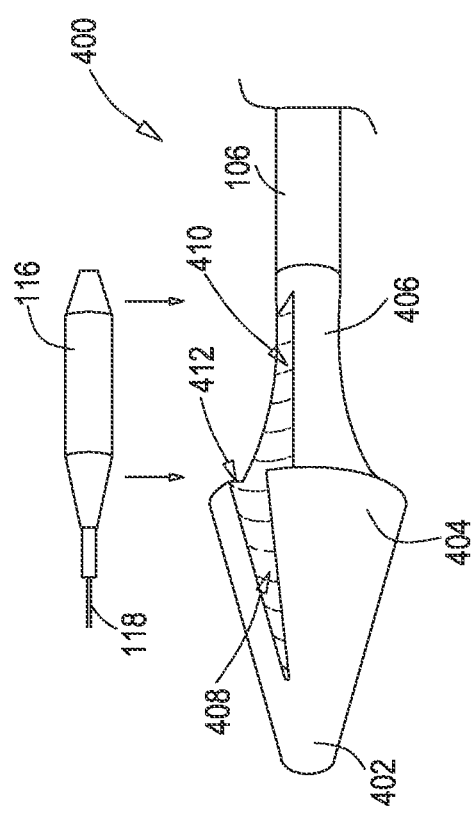
FIG. 15 shows an example of a tunneling tip having a slot for receiving an extension connector.

FIG. 15 shows an example of a tunneling tip 400 with a stem portion 406 attached to the shaft 106. The tunneling tip includes a blunt point 402 and a body 404 with a conical shape for tunneling. A longitudinal slot 408 is present within the tip 400 so that the connector 116 may be positioned into a rear portion 410 of the slot 408, behind the large diameter area 412 of the tip 400. The slot portion 410 retains the connector 116 during the pull-through procedure.

Figure 16:
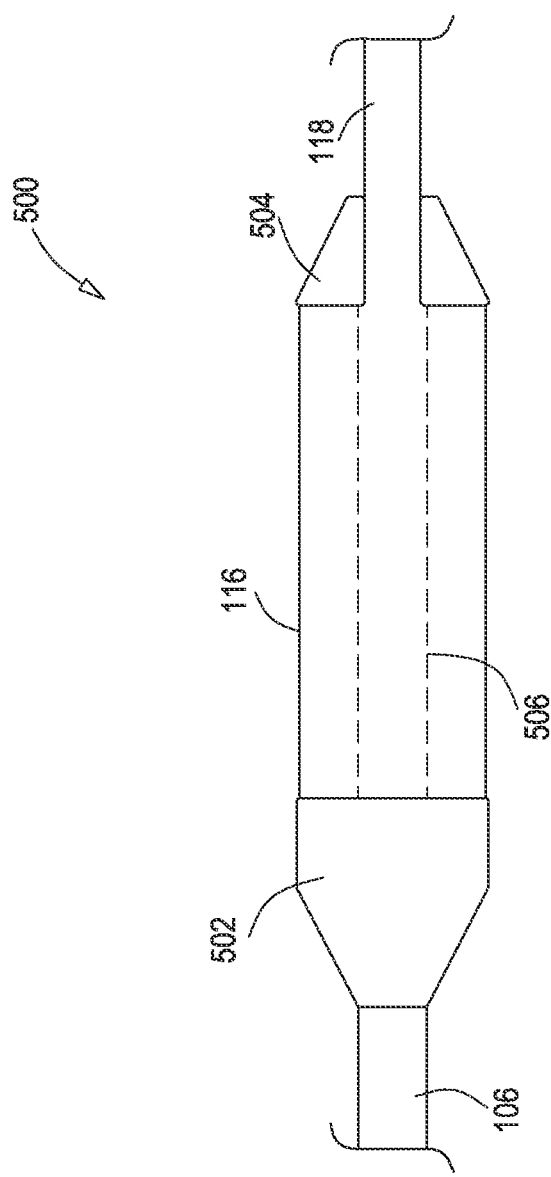
FIG. 16 shows an example of a carrier with a reduced structure.

FIG. 16 shows an example of a tip in the form of a carrier 500 attached to the shaft 106. The carrier 500 includes a first portion 502 at the shaft 106 and a second portion 504 on the opposite end. Both the first portion 502 and the second portion 504 define receptacles that receive the lead extension connector 116. A strip 506 is present to couple the first portion 502 to the second portion 504. The strip 506 may be flexible to aid in positioning the connector 116 within the receptacles of portions 502, 504.

Figure 17:
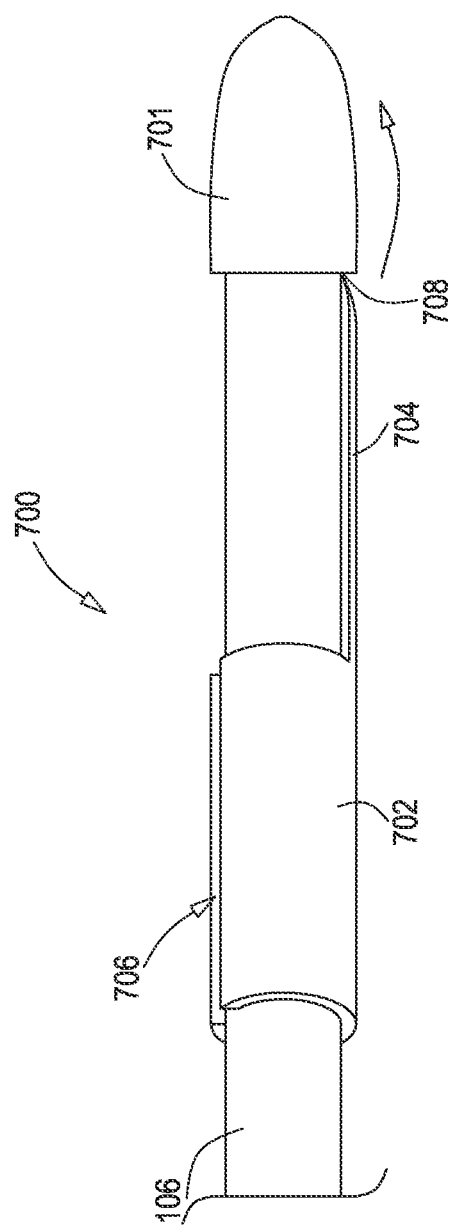
FIG. 17 shows an example of a carrier that is tethered and attached to the tunneling tool during tunneling.
Figure 18:
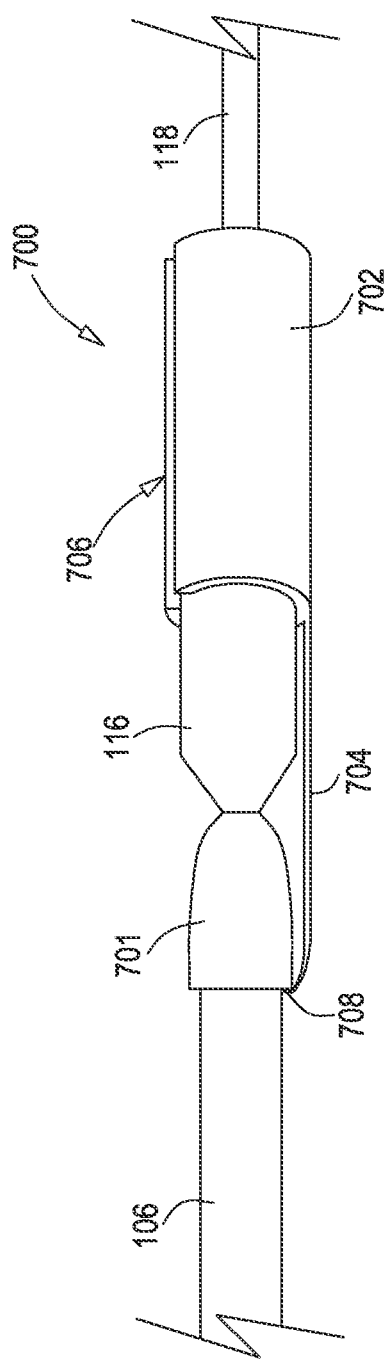
FIG. 18 shows the carrier of FIG. 17 after being detached from the tunneling tool and attached to an extension connector while remaining tethered to the tunneling tool.

FIG. 17 shows an example of a tip in the form of a combination tunneling tip 701 and carrier 700. The carrier 700 includes a body portion 702 that has a slot 706 that allows the body portion 702 to snap onto and off of the shaft 106. The body portion 702 is tethered to the shaft 706 via a tether strip 704. During tunneling, the body 702 remains attached to the shaft 106. For the pull-through procedure, the body 702 is removed from the shaft 106 and is attached onto the connector 116, as shown in FIG. 18.

Figure 19:
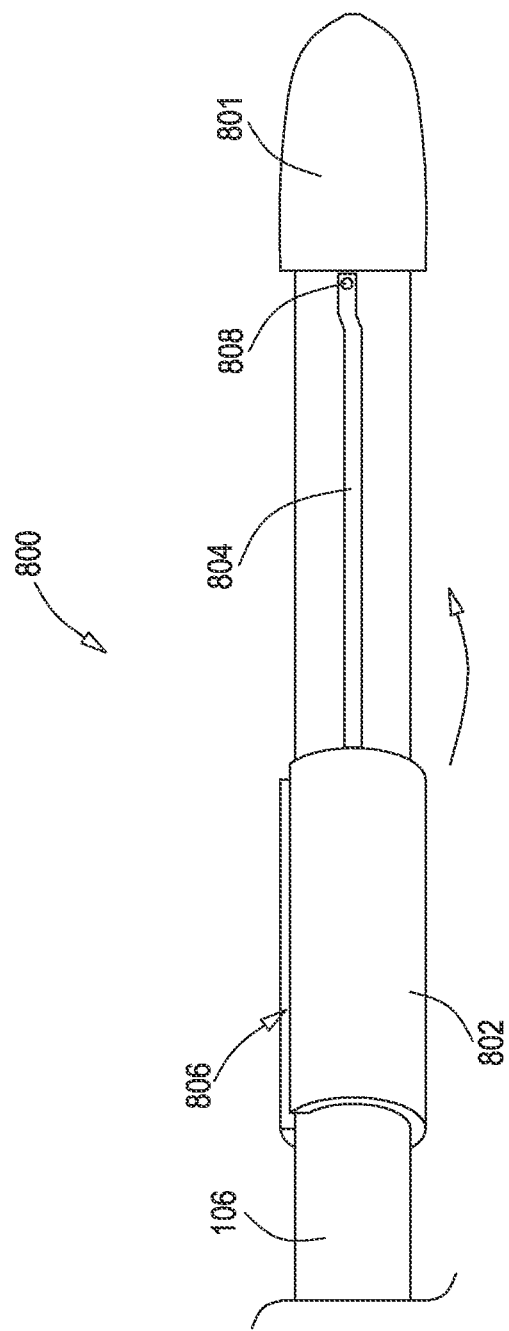
FIG. 19 shows an example of a carrier that is attached to the tunneling tool and pivotably connected to the tunneling tool during tunneling.
Figure 20:
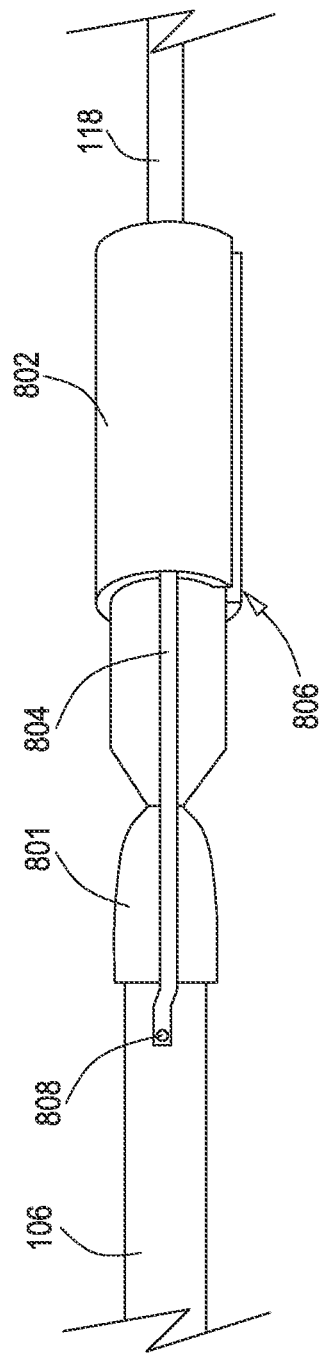
FIG. 20 shows the carrier of FIG. 19 after being detached from the tunneling tool and being pivoted while being attached to an extension connector.

FIG. 19 shows an example of a tip in the form of a combination tunneling tip 801 and carrier 800. The carrier 800 includes a body portion 802 that has a slot 806 that allows the body portion 802 to snap onto and off of the shaft 106. The body portion 802 is also pivotably attached to the shaft 106 via arm 804. A similar arm may also be present on the backside of the shaft 106. The arm 804 has a pivot point 808. During tunneling, the body 802 remains attached to the shaft 106. For the pull-through procedure, the body 802 is removed from the shaft 106, is pivoted 180 degrees and is attached onto the connector 116, as shown in FIG. 18.

Figure 21:
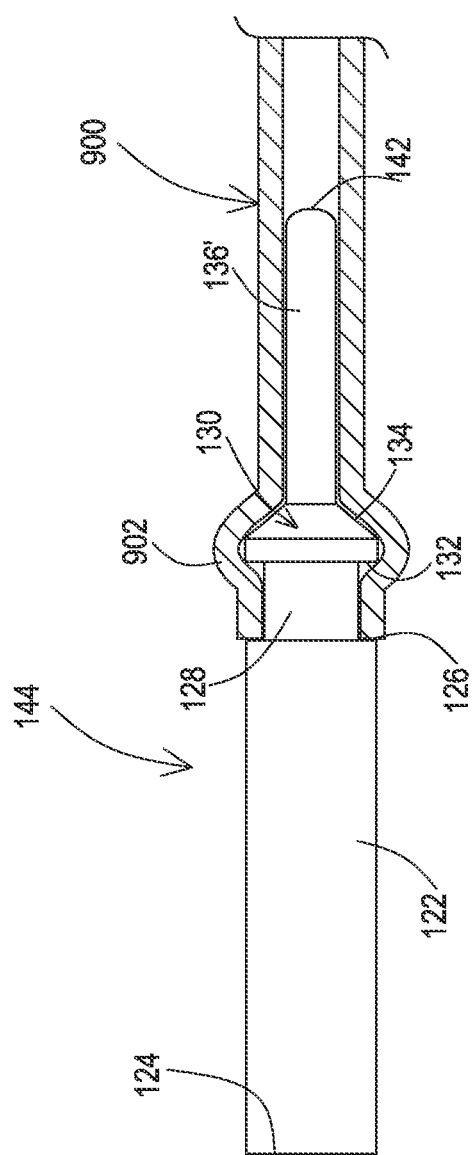
FIG. 21 shows an exemplary cross-sectional view of a catheter extension body with the tip including the pin and barb inserted into the catheter extension body.

FIG. 21 shows an additional use for a structure such as the pin 144 of FIG. 5. Here, a catheter extension body 900 is being pulled through a subcutaneous tunnel. The end 142 of the pin 144 is inserted into the bore of the catheter extension body 900. The barb 130 engages a compliant distal portion 902 of the catheter extension body 900. Thus, the pin 144 can apply a pulling force while relying on the engagement of the barb 130 to the distal portion 902 to pull the catheter extension body 900 through the tunnel.

While embodiments have been particularly shown and described, it will be understood by those skilled in the art that various other changes in the form and details may be made therein without departing from the spirit and scope of the invention.

What is claimed is:

1. A tool for pulling an implantable medical lead extension through a subcutaneous tunnel, comprising:
   a handle;
   a shaft having a first end and a second end, the first end being coupled to the handle;
   a tip coupled to the second end of the shaft, the tip comprising a pin having a first end that is sized to be inserted into a bore of a connector body located on a distal end of the implantable lead extension and the tip comprising a second end, the tip further comprising a barb positioned on the pin and spaced axially from the first end of the pin, the barb being sized to create an interference fit within a compliant distal portion of the connector body, the barb having a first barb portion that slopes from a largest barb diameter to a smallest barb diameter where the smallest diameter of the barb is closer to the first end of the tip than the largest diameter of the barb, and the barb has a second portion that extends axially from the first portion towards the second end of the tip that is opposite the first end the second end of the tip being attached to the shaft, and with the second barb portion being the largest barb diameter, the second end of the tip having a diameter at the attachment to the shaft equal to the largest diameter of the barb, wherein the tip further comprises a first pin section and a second pin section, the second pin section comprising a first section end that is blunt and the first section end that is blunt has a larger diameter than an entire axial length of the first pin section, and the second pin section further comprising a second section end where the second section end provides the second end of the pin, the second pin section having a constant diameter from the first section end to the second section end, the first pin section interconnecting the second portion of the barb and the first section end of the second pin section where the first pin section has a diameter larger than the smallest diameter of the barb and smaller than the largest diameter of the barb.

2. The tool of claim 1, wherein the handle and shaft are constructed in a unitary manner.

3. The tool of claim 2, wherein the tip is detachable from the second end of the shaft.

4. The tool of claim 3, wherein the pin includes a first section positioned axially between the barb and the first end having a first diameter, a second section positioned axially between the first section and the first end so as to align with a set screw within the bore of the connector body, the second section having a second diameter that is smaller than the first diameter of the first section.

5. The tool of claim 1, wherein the barb is blunt on a side closer to the shaft.

6. The tool of claim 5, wherein the tip is constructed of a biocompatible metal.

7. The tool of claim 1, wherein the second portion of the barb extends axially with a constant diameter from the first portion toward the second end of the tip.

8. A tool for pulling an implantable medical lead extension through a subcutaneous tunnel, comprising:
   a handle;
   a shaft having a first end and a second end, the first end being coupled to the handle; and
   a tip coupled to the second end of the shaft, the tip comprising a pin having a first end that is sized to be inserted into a bore of a connector body located on a distal end of the implantable lead extension and the tip comprising a second end, the tip further comprising a barb positioned on the pin and spaced axially from the first end of the pin, the barb being sized to create an interference fit within a compliant distal portion of the connector body, the barb having a first barb portion that slopes from a largest barb diameter to a smallest barb diameter where the smallest diameter of the barb is closer to the first end of the tip than the largest diameter of the barb, and the barb has a second portion that extends axially from the first portion towards the second end of the tip that is opposite the first end the second end of the tip being attached to the shaft, and with the second barb portion being the largest barb diameter, the second end of the tip having a diameter at the attachment to the shaft equal to the largest diameter of the barb, wherein the tip further comprises a first pin section and a second pin section, the second pin section comprising a first section end that is blunt and a second section end where the second section end provides the second end of the pin, the first pin section directly interconnecting the second portion of the barb and the first section end of the second pin section where the first pin section has a diameter larger than the smallest diameter of the barb and smaller than the largest diameter of the barb and where the first pin section has a constant diameter for an entire distance between the second portion of the barb and the first section end of the second pin section and where the second pin section has a constant diameter from the first section end to the second section end.

9. The tool of claim 8, wherein the second portion of the barb extends axially with a constant diameter from the first portion toward the second end of the tip.

10. A tool for pulling an implantable medical lead extension through a subcutaneous tunnel, comprising:

a handle;
a shaft having a first end and a second end, the first end being coupled to the handle; and
a tip coupled to the second end of the shaft, the tip comprising a pin having a first end that is sized to be inserted into a bore of a connector body located on a distal end of the implantable lead extension and the tip comprising a second end, the tip further comprising a barb positioned on the pin and spaced axially from the first end of the pin, the barb being sized to create an interference fit within a compliant distal portion of the connector body, the barb having a first barb portion that slopes from a largest barb diameter to a smallest barb diameter where the smallest diameter of the barb is closer to the first end of the tip than the largest diameter of the barb, and the barb has a second portion that extends axially from the first portion towards the second end of the tip that is opposite the first end the second end of the tip being attached to the shaft, and with the second barb portion being the largest barb diameter, the second end of the tip having a diameter at the attachment to the shaft equal to the largest diameter of the barb, wherein the tip further comprises a first pin section and a second pin section, the second pin section comprising a first section end that is blunt and faces the first end, and the second pin section further comprising a second section end where the second section end provides the second end of the pin, the first pin section interconnecting the second portion of the barb and the first section end of the second pin section.

11. The tool of claim 10, wherein the second portion of the barb extends axially with a constant diameter from the first portion toward the second end of the tip.

* * * * *